United States Patent [19]

Johnson

[11] Patent Number: 5,513,629
[45] Date of Patent: May 7, 1996

[54] MICROWAVABLE HEAT RELEASING AND ABSORBING COMPOSITION AND CONTAINER

[75] Inventor: Michael L. Johnson, Oak Grove, La.

[73] Assignee: Dura Therm Inc., Oak Grove, La.

[21] Appl. No.: 375,724

[22] Filed: Jan. 20, 1995

[51] Int. Cl.[6] ............................................. F24J 1/00
[52] U.S. Cl. ............................. 126/263.01; 126/263.02; 126/263.07; 252/70; 607/114; 604/368
[58] Field of Search ........... 126/263.01, 263.02–263.07; 252/70; 607/114; 604/368

[56] References Cited

U.S. PATENT DOCUMENTS

| | | |
|---|---|---|
| 1,819,807 | 8/1931 | Baysinger . |
| 3,804,077 | 4/1974 | Williams . |
| 3,913,559 | 10/1975 | Dandiker . |
| 4,596,250 | 6/1986 | Beisang, III et al. . |
| 4,671,267 | 6/1987 | Stout . |
| 4,756,311 | 7/1988 | Francis, Jr. . |
| 4,886,063 | 12/1989 | Crews .................................... 128/403 |
| 5,150,707 | 9/1992 | Anderson . |

FOREIGN PATENT DOCUMENTS

| | | |
|---|---|---|
| 4204528 | 9/1992 | Germany . |
| 61-276556 | 12/1986 | Japan . |

Primary Examiner—Larry Jones
Attorney, Agent, or Firm—Richard C. Litman

[57] ABSTRACT

A microwavable heat releasing and absorbing composition comprises paraffin wax, distilled water, polyacrylamide, mineral oil, glycerin, polypropylene glycol, acid and corn starch. By variation of the relative ratios of the components, the composition can take on a variety of consistencies and viscosities. The composition is capable of retaining its temperature for an extended period of time despite surrounding variations in temperature. It is also capable of maintaining its pliability and consistency over a wide range of temperatures. The composition has a high vapor point and is well-suited for heating in a microwave oven, or cooling in a freezer. The composition when placed in a suitable container can be used in hot-and-cold packs, as well a variety of other applications. Preferably, the container is enclosed in a vinyl package with transverse ribs.

10 Claims, 1 Drawing Sheet

MICROWAVABLE HEAT RELEASING AND ABSORBING COMPOSITION AND CONTAINER

BACKGROUND OF THE INVENTION

1. Field of the Invention

The present invention relates generally to heat sources and heat withdrawing sources, and more particularly to heat sources and heat withdrawing sources capable of being heated by microwave energy.

2. Description of the Prior Art

Frequently, there is a need to provide localized heat to some object, and it is often inconvenient to move the object close to an immobilized heat source such as a heat vent in a building's heating system. Many attempts have been made to provide a heat source that can readily be moved to the object to be heated. Likewise, there is frequently a need to withdraw heat from an object, and the same problems develop as with heat sources. Similar efforts have been made to rectify these problems encountered in heat withdrawing apparatuses. The typical results of all these efforts are temperature buffering substances that are contained in portable hot packs, cold packs, or hot-and-cold packs. Usually, such a substance is comprised by various component substances, some of which are best suited for giving off heat, whereas others are best suited for absorbing heat, or providing some other desirable characteristics. All of these previous substances fail in one way or another to provide an inexpensive, convenient, readily manufactured solution to the need for a portable heat realeasing and withdrawing substance. Moreover, prior substances and containers for holding them are less than ideally suited for convenient heating in a microwave oven.

U.S. Pat. No. 1,819,807, issued on Aug. 18, 1931, to Virgil R. Baysinger, discloses a exothermic chemical reactant mixture for use in hot packs. The mixture gives off heat when water is applied. The invention is largely comprised by cast iron, a relatively dense material, and thus tends to be heavy relative to the amount of surface area covered. Such heaviness could make the invention unusable in circumstances where undue pressure on the article or body part to be heated must be avoided. Also, the mixture requires an external source of oxygen and water for heat production, and hence is unusable where these substances are unavailable. The mixture also wears out after 80 to 100 hours of use, and thus has no lasting value. Moreover, the invention is not suited for acting as a heat withdrawing source, and cannot be heated in a microwave oven.

U.S. Pat. No. 3,804,077, issued on Apr. 16, 1974, to Veron L. Williams, discloses a hot pack containing an exothermic, gel-forming reactant mixture, and a cold pack containing an endothermic, gel-forming reactant mixture. These packs have a life span limited by the duration of the chemical reaction that produces or absorbs heat. Once used, they cannot practically be re-used. Also, the packs are not suitable for heating by microwave energy.

U.S. Pat. No. 3,913,559, issued on Oct. 21, 1975, to Walter B. Dandiker, shows a constant temperature device that remains at its heat of fusion temperature while it either gives off or absorbs heat. Such a device is not necessarily capable of giving off or absorbing heat subsequent to freezing or melting, respectively, especially when capable of rapid heating or cooling, as the patent discloses. Additionally, such a device is only functional as described when its heat of fusion is the temperature desired by the user. Thus, the device is not adaptable to a variety of applications. The patent lists a variety of substances, none of which is part of the applicant's invention; and none of the substances used in the applicant's invention, other than acid, is disclosed in the Dandiker patent. Moreover, there is no indication in the patent that the patented invention can or should be heated in a microwave oven.

U.S. Pat. No. 4,596,250, issued on Jun. 24, 1986, to Arthur A. Beisang, III, et al., discloses a hot-and-cold pack that retains its temperature and moldability for an extended period of time. It is intended to be capable of autoclaving, and is not designed to be heated by microwave energy. In fact, when the suggested metal-coated layer or metal particles are included, the invention would be entirely unsuitable for heating in a microwave oven. Additionally, the invention does not disclose use of a humectant, such as glycerin, polyacrylamide, mineral oil, corn starch, acid or polypropylene glycol.

U.S. Pat. No. 4,671,267, issued on Jun. 9, 1987, to Edward I. Stout, discloses a substance that retains is pliability over a wide temperature range and is intended to be heated in a microwave oven. The invention comprises a humectant, such as glycerin, entrapped in a polymer matrix, such as one comprised by acrylic acid or acrylamide monomer moieties. The invention does not disclose the use of paraffin wax, mineral oil, corn starch, or polypropylene glycol.

U.S. Pat. No. 4,756,311, issued on Jul. 12, 1988, to Sam E. Francis, Jr., shows a microwavable hot-and-cold pack including an aqueous gel. This gel does not include glycerin, polyacrylamide, paraffin wax, mineral oil, acid or corn starch.

U.S. Pat. No. 5,150,707, issued on Sep. 29, 1992, to Leslie B. Anderson, shows a hot-and-cold pack including a microwavable gel. The gel is comprised by an acrylic resin that absorbs many times its dry weight. The resin is in particulate form and bound to a substrate until water is applied. Because of the necessity for user-application of water, use of the device is limited to locations where water is readily available. Moreover, there is no teaching on the patent for the use of glycerin or other humectant, a polymer, paraffin wax, mineral oil, acid or corn starch.

German Patent 4,204,528, issued on Sep. 24, 1992, to Klaus Peter Kayser, discloses a paraffin-filled bag for use as a hot pack. There is no teaching in the patent for the use of glycerin or other humectant, polyacrylamide, mineral oil, acid or corn starch.

Japanese Patent 61-276556, issued on Dec. 6, 1986, to Jiryokusenko Nippon, discloses a low cost stomach warmer comprised by alumina and silica. Because of this composition, it would be unsuitable for heating in a microwave oven.

None of the above prior art references discloses the use of transverse ribs in a hot pack container for limiting puffing during heating in a microwave oven and for maintaining integrity of the container.

None of the above inventions and patents, taken either singly or in combination, is seen to describe the instant invention as claimed.

SUMMARY OF THE INVENTION

The present invention provides a microwavable heat releasing and absorbing composition comprising paraffin wax, distilled water, polyacrylamide, mineral oil, glycerin, polypropylene glycol, acid and corn starch. By variation of the relative ratios of the components, the composition can take on a variety of consistencies and viscosities. The composition has a high effective specific heat, and thus is capable of retaining its temperature for an extended period of time despite surroundng variations in temperature. It is also capable of maintaining its consistency over a wide range of temperatures. The composition has a high vapor point and is well-suited for heating in a microwave oven, or cooling in a freezer. The invention can be used in hot-and-cold packs, as well as variety of other applications. Preferably, it is enclosed in a vinyl package with transverse ribs.

Accordingly, it is a principal object of the invention to provide a microwavable composition that will absorb and release a substantial amount of heat.

It is another object of the invention to provide a composition which avoids vaporization, even when heated rapidly in a microwave oven to a temperature near the boiling point of water.

It is a further object of the invention to provide a composition, the consistency, texture, and pliability of which can be varied by variation of the relative ratio of components.

Yet a further object of the invention is to provide a composition having a consistency such that it will not spill out of a container containing it, even if the container is ruptured.

Yet another object of the invention is to provide a composition that will retain a moisture storing substance in uniform distribution.

A still further object of the invention is to provide a microwavable heating and cooling composition in a container constructed in such a way that the container maintains its integrity and the composition avoids puffing, despite microwaving.

Yet a further object of the invention is to provide a composition that will not deteriorate or become unusable, despite repeated, frequent, rapid heatings to high or non-uniform temperatures.

Still another object of the invention is to provide a composition that will not freeze or lose pliability even when its temperature is reduced substantially below room temperature.

It is an object of the invention to provide improved gel compositions and a container thereof suitable for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 3:
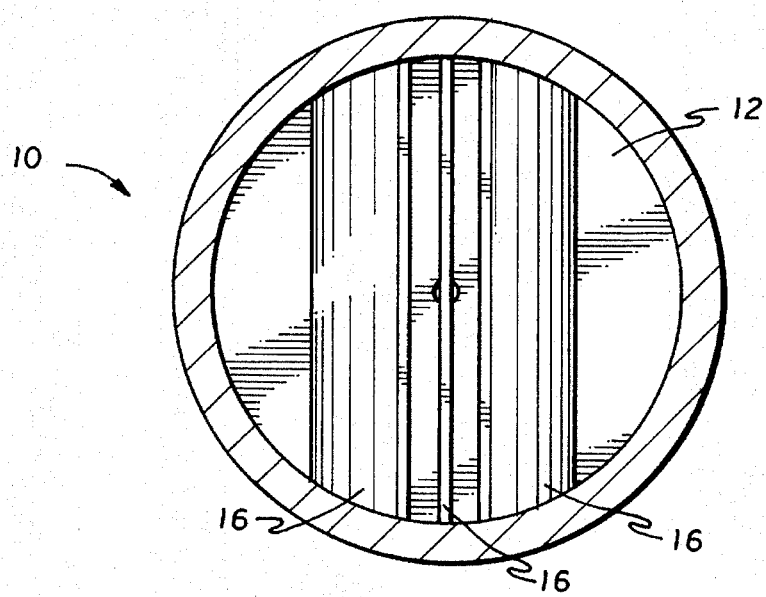
FIG. 3 is a top cut-away view of a container suitable for containing the present composition, showing a top view of the container's ribs.
Figure 2:
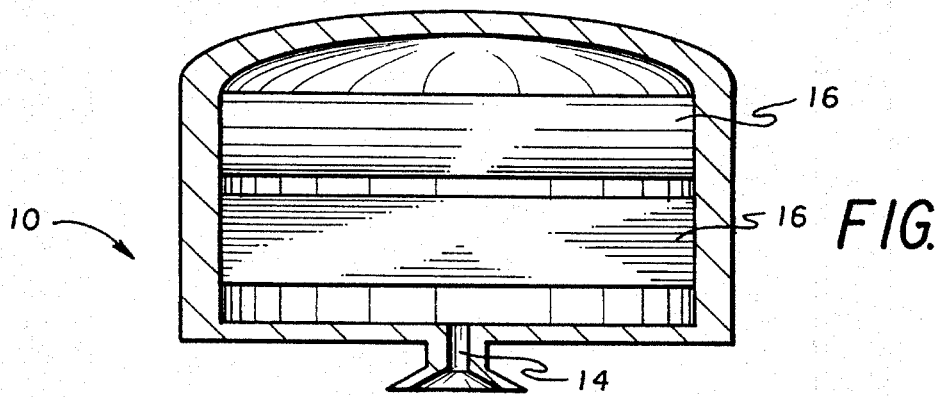
FIG. 2 is a side cut-away view of a container suitable for containing the present composition, showing a side-view of two of the container's ribs.
Figure 1:
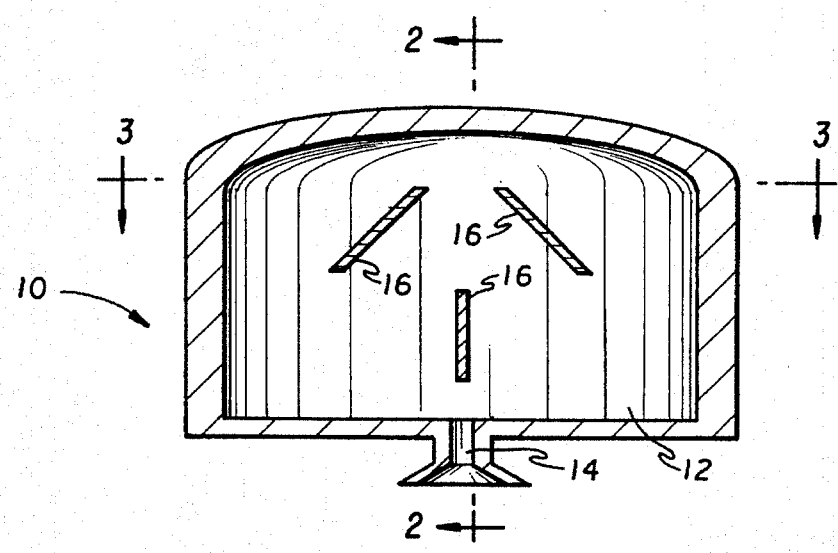
FIG. 1 is a side cut-away view of a container suitable for containing the composition of the present invention, showing sections of the container's ribs.

The present invention comprises a unique composition suitable for either releasing or absorbing heat, depending on the circumstances in which it is used, and capable of being heated in a microwave oven. Also included is a container suitable for containing the composition during such heating.

Referring to the drawings, a container 10 has an open interior 12. There is a filler tube 14 closable by any known means (not shown) and a plurality of ribs 16 extending entirely across the open interior 12. Preferably, the container 10 is made from an impermeable synthetic material such as vinyl. In this way, the contents (not shown) of the container 10 are prevented from seeping out of the container 10. Varying the shape and size of the container 10 makes possible the application of the container 10 and contents to a variety of objects (not shown), for a variety of purposes and uses.

Within the interior 12 of the container 10, there is a temperature buffering composition (not shown). Preferably, this composition includes paraffin, glycerin, mineral oil, polyacrylamide, cornstarch, water, acetic acid, and polypropylene glycol. This composition exhibits extraordinary characteristics not seen in prior compositions. For example, this composition retains its temperature for a much longer period than prior compositions. Additionally, this composition can be heated in a microwave oven (not shown) to 180 degrees Fahrenheit without exhibiting any puffing. In fact, it can be heated in a microwave oven to 336 degrees Fahrenheit without exhibiting any deterioration. Furthermore, the consistency of this composition and the presence of gel-sealing paraffin wax mean that the composition will not spill out of a container 10, even if the integrity of the container 10 is breached, e.g. by a hole or tear.

In regard to the component characteristics of the present composition, the relative ratios of components can vary. However, typically the composition primarily comprises glycerin, which acts as a humectant. The next most voluminous components are water, which serves to bring the various components into a soft and pliable condition, and polypropylene glycol, which lowers the freezing point of the composition, thereby allowing for pliability even at low temperatures. Also present in substantial volume is polyacrylamide, which acts as an absorbent component. Cornstarch is added to bind the components together. Mineral oil is also present in a substantial amount and serves to maintain the temperature of the composition to a greater extent than would otherwise be the case. Present in lesser amounts are paraffin wax, which seals the gel composition to prevent staining in case of container-rupture, and acetic acid, which along with water serves to bring the various components into a soft and pliable condition.

The following table (Table I) sets forth the approximate ranges of use for the components in the most preferred formulations:

TABLE I

| Component | Range |
| --- | --- |
| Paraffin Wax | 1.0% to 6.3% * |
| Glycerin | 50.1% to 75.5% # |
| Mineral Oil | 6.2% to 10.5% # |
| Polyacrylamide | 12.5% to 45.1% * |
| Corn Starch | 6.2% to 14.25% * |
| Water | 0.5% to 45.25% # |
| Acetic Acid | 1.0% to 17.0% # |
| Polypropylene Glycol | 0.5% to 45.25% # |

* By weight
By volume

An example of a preferred formulation of the inventive composition is as shown in the following table (Table II):

TABLE II

| Component | Amount |
|---|---|
| Paraffin Wax | 6.27%* |
| Glycerin | 50.17%# |
| Mineral Oil | 6.27%# |
| Polyacrylamide | 12.54%* |
| Corn Starch | 6.27%* |
| Water | 0.84%# |
| Acetic Acid | 16.81%# |
| Polypropylene Glycol | 0.84%# |

\* By weight
\# By volume

By adjusting the proportions of the composition, the consistency of the composition can be varied. It may have any consistency from a syrupy consistency to a hard rubber-like consistency. Because of the remarkable variation possible, the invention can be used for passive heat and cold applications, for simultaneous exercise and heating of hands, or for many other purposes. The omission of polypropylene glycol to the composition will bring about a composition primarily useful for heating applications.

Because the container 10 for holding the composition is preferably made of vinyl, none of the components of the composition will escape under normal use, thereby ensuring that moisture and oil within the composition will not stain or otherwise affect clothing or other surfaces which might come into contact with the invention. For manufacturing purposes, all the components of the composition, except for water and acetic acid, would preferably be injected into the container 10 through the filler tube 14. Preferably, the water and acetic acid would then be added to initiate a softening and increased pliability of the total composition. The filler tube would then be closed by any suitable, known means (not shown).

In use, the composition in the container can be heated by placement in a microwave for a predetermined number of minutes sufficient to warm the composition to the desired temperature under 180 degrees Fahrenheit. This high temperature limit attests to the composition's ability to avoid puffing when heated in a microwave oven. Alternately, the composition in the container 10 can be cooled to any desired temperature (greater than absolute zero) by placement in a freezer. Once at the desired temperature, the composition in the container 10 can be applied to manifold objects for any number of purposes related to heating or cooling such objects, including, but not limited to, known orthopedic purposes.

While the present invention has been described with respect to the presently preferred embodiment, it should be understood that the present invention is not limited to the sole embodiment described above, but encompasses any and all embodiments within the scope of the following claims.

I claim:

1. A microwavable heat releasing and absorbing gel composition having a pliable consistency over a predetermined range of temperatures, said composition comprising: a humectant, a freezing-point depressant, a gel-sealer, polyacrylamide as an absorbent material, cornstarch as a binder, mineral oil as a component for increasing specific heat, and components for initiating pliability.

2. The composition according to claim 1, wherein:
   said humectant is glycerin, and
   said freezing-point depressant is polypropylene glycol.

3. The composition according to claim 1, wherein said gel-sealer is paraffin wax.

4. The composition according to claim 1, wherein said components for initiating pliability include water and acid.

5. The composition according to claim 4, wherein said acid is acetic acid.

6. A portable hot-and-cold device containing a composition according to claim 1.

7. A pack according to claim 6 further comprising an outer skin impermeable to said temperature buffering mixture, said skin having an inner surface and defining a partially closed container containing a space, said space filled with said temperature buffering mixture.

8. The pack according to claim 7, wherein:
   said outer skin has a closable filler tube;
   transverse ribs attach to a portion of said inner surface of said skin, extend through said space, and reattach to another portion of said surface.

9. A method of using a composition according to claim 1, comprising the steps of:
   injecting into a container said humectant, said freezing-point depressant, said gel-sealer, said absorbent material, said binder, said component for increasing specific heat;
   subsequently adding said components for initiating pliability.

10. A method of using a composition according to claim 9, further comprising the steps of:
   formulating said ingredients so that said mixture has a firm consistency;
   heating said composition to a temperature above human body-temperature;
   kneading said composition in a human hand for the purpose of exercise.

* * * * *